US012239786B2

(12) United States Patent
Nye

(10) Patent No.: US 12,239,786 B2
(45) Date of Patent: *Mar. 4, 2025

(54) SYSTEMS AND METHODS FOR TREATING AN AIRWAY

(71) Applicant: Hoyt Medical LLC, Sunfish Lake, MN (US)

(72) Inventor: Hoyt Nye, Sunfish Lake, MN (US)

(73) Assignee: Hoyt Medical LLC, Sunfish Lake, MN (US)

( * ) Notice: Subject to any disclaimer, the term of this patent is extended or adjusted under 35 U.S.C. 154(b) by 478 days.

This patent is subject to a terminal disclaimer.

(21) Appl. No.: 17/005,707

(22) Filed: Aug. 28, 2020

(65) Prior Publication Data

US 2021/0113799 A1    Apr. 22, 2021

Related U.S. Application Data

(63) Continuation of application No. 14/795,531, filed on Jul. 9, 2015, now Pat. No. 10,758,694.

(51) Int. Cl.
*A61M 16/04* (2006.01)
*A61M 16/08* (2006.01)

(52) U.S. Cl.
CPC .... *A61M 16/0463* (2013.01); *A61M 16/0816* (2013.01); *A61M 16/0409* (2014.02); *A61M 2202/0208* (2013.01)

(58) Field of Classification Search
CPC ....................... A61M 16/0463; A61M 16/0816
See application file for complete search history.

(56) References Cited

U.S. PATENT DOCUMENTS

| | | | | |
|---|---|---|---|---|
| 3,319,628 A | * | 5/1967 | Halligan | A61M 1/7411 433/91 |
| 3,767,233 A | * | 10/1973 | Hodge | F16L 33/30 285/239 |
| 3,991,762 A | | 11/1976 | Radford | |
| 4,022,218 A | * | 5/1977 | Riddick | A61M 1/84 604/266 |
| 4,112,940 A | * | 9/1978 | Parkes | A61M 16/201 128/205.24 |
| 4,193,406 A | | 3/1980 | Jinotti | |
| 4,270,778 A | * | 6/1981 | Brownell | A61M 16/0463 128/207.14 |
| 4,307,903 A | * | 12/1981 | Wallace | A61M 39/1011 128/207.14 |

(Continued)

FOREIGN PATENT DOCUMENTS

| | | | | |
|---|---|---|---|---|
| GB | 2111394 | | 7/1983 | |
| GB | 2111394 A | * | 7/1983 | ............ A61M 16/04 |

(Continued)

OTHER PUBLICATIONS

Extended European Search Report in Application No. 16821806.3, dated Jul. 9, 2018, 6 pages.

(Continued)

*Primary Examiner* — Kathryn E Ditmer
(74) *Attorney, Agent, or Firm* — Fish & Richardson P.C.

(57) ABSTRACT

Some embodiments described herein may include a system or a method in which an air delivery lumen of an endotracheal tube, a laryngeal mask, or other airway device is configured to optionally provide a suction effect.

21 Claims, 7 Drawing Sheets

(56) References Cited

U.S. PATENT DOCUMENTS

| | | | |
|---|---|---|---|
| 4,351,328 A | 9/1982 | Bodai | |
| 4,534,542 A * | 8/1985 | Russo | A61M 1/7411 D24/129 |
| 4,589,684 A * | 5/1986 | Nowacki | F16L 37/098 285/423 |
| 4,673,398 A * | 6/1987 | Turner | A61M 1/84 604/902 |
| 4,729,765 A * | 3/1988 | Eckels | A61M 1/7411 604/119 |
| 4,774,940 A | 10/1988 | Linder | |
| 4,852,563 A | 8/1989 | Gross | |
| 4,881,542 A * | 11/1989 | Schmidt | A61M 16/0486 128/207.14 |
| 5,279,549 A | 1/1994 | Ranford | |
| 5,509,408 A * | 4/1996 | Kurtis | A61M 16/0486 128/207.14 |
| 5,713,348 A | 2/1998 | Pell | |
| 5,730,727 A * | 3/1998 | Russo | A61M 1/7411 604/118 |
| 6,500,164 B1 * | 12/2002 | Turner | A61M 1/84 604/403 |
| 6,958,050 B1 * | 10/2005 | Choski | A61M 1/00 604/35 |
| 7,802,574 B2 * | 9/2010 | Schultz | A61M 16/0463 128/207.14 |
| 8,499,763 B2 | 8/2013 | Ledwith | |
| 2002/0005197 A1 | 1/2002 | DeVries | |
| 2003/0153897 A1 | 8/2003 | Russo | |
| 2006/0225741 A1 * | 10/2006 | Rothman | A61M 16/04 128/207.14 |
| 2007/0023050 A1 | 2/2007 | Janatpour | |
| 2008/0236590 A1 | 10/2008 | Reissmann | |
| 2011/0139151 A1 | 6/2011 | Burns | |
| 2011/0197895 A1 * | 8/2011 | Stephenson | A61M 16/0488 128/207.14 |
| 2011/0282326 A1 * | 11/2011 | Krupa | A61M 1/74 604/540 |
| 2012/0239435 A1 | 9/2012 | Ennett | |
| 2012/0272955 A1 | 11/2012 | Cool | |
| 2014/0096766 A1 | 4/2014 | Avitsian et al. | |

FOREIGN PATENT DOCUMENTS

| | | |
|---|---|---|
| JP | H07323088 | 12/1995 |
| JP | 2004283329 | 10/2004 |
| JP | 2008161672 | 7/2008 |
| JP | 2008295591 | 12/2008 |
| JP | 2013180049 | 9/2013 |
| JP | 2013192657 | 9/2013 |
| WO | WO 1994002191 | 2/1994 |
| WO | WO 1998024500 | 6/1998 |
| WO | WO 2013063520 | 5/2013 |
| WO | WO 2013116670 | 8/2013 |

OTHER PUBLICATIONS

International Preliminary Report on Patentability in International Application No. PCT/US2016/039305, mailed Jan. 18, 2018, 8 pages.

International Search Report and Written Opinion for PCT/US2016/039305, mailed Sep. 19, 2016, 21 pages.

Tibble, Adam, et al. "A Universal Airway Circuit Cap Connector (Tibblecap)". Department of Anesthesiology, University of California San Diego; 2011. (2 pages).

* cited by examiner

SYSTEMS AND METHODS FOR TREATING AN AIRWAY

CROSS-REFERENCE TO RELATED APPLICATIONS

This application is a continuation of and claims priority to U.S. application Ser. No. 14/795,531, filed on Jul. 9, 2015, the entire contents of which are hereby incorporated by reference.

TECHNICAL FIELD

This document relates to systems and methods for treating a patient's airway, including for example, a system or method in which an endotracheal tube, a laryngeal mask, or other airway device is configured to optionally provide a suction effect (e.g., to aid in removal of blood and/or secretions in a patient's throat region) when the endotracheal tube, the laryngeal mask, or the other airway device is removed.

BACKGROUND

Certain medical procedures, for example, an anesthetic procedure, require establishing and maintaining a patient's airway. During such procedures, a patient may be intubated with an endotracheal tube, or have a laryngeal mask placed into his or her mouth cavity to cover the laryngeal inlet for lung ventilation or delivery of other gaseous flow. In some cases, a patient undergoes an endotracheal intubation procedure in which an endotracheal tube is placed into and advanced through the patient's mouth and into the trachea. The endotracheal tube can be inserted under direct vision, by use of a laryngoscope, to provide visual confirmation of the endotracheal tube position within the trachea, minimizing potential trauma to surrounding tissues and anatomical structures. In other cases, the laryngeal mask can be used to ventilate a patient's lung by placing an elliptical mask into the patient's mouth, positioning the elliptical mask over the supraglottic structures within the hypopharynx region, and deploying the elliptical mask using a cuff connector to create an airtight seal over the glottis.

In some traditional practices, at the end of the anesthetic procedure or other medical procedure that involves an endotracheal tube or a laryngeal mask, a separate suction tool or catheter, such as a Yankauer suction tip, which is sized differently from the endotracheal tube or laryngeal mask, is advanced into the patient's throat region in an attempt to remove accumulated secretions and/or blood from the pharynx and posterior pharynx prior to the removal of the endotracheal tube or the laryngeal mask. In such circumstances, the practitioner may not be able to visualize or otherwise confirm that the suction tool or catheter is sufficiently removing secretions in the pharynx and posterior pharynx.

SUMMARY

Some embodiments described herein may include a system configured to provide a suction effect to an air delivery lumen of an endotracheal tube, a laryngeal mask, or other airway device. Such a configuration can be useful, for example, to aid in removal of blood and/or secretions in a patient's throat region (including the pharynx, posterior pharynx, or both) during the removal of the intubation tubing or other airway instrument that was previously inserted into the patient's throat as part of the anesthetic procedure or other medical procedure. In particular implementations in which an endotracheal tube or a laryngeal mask was used during an anesthetic procedure or other procedure that involved delivery of gaseous flow into a patient, the system described herein may optionally include at least an airway adapter device that is shaped and structurally configured to sealably connect with the endotracheal tube or laryngeal mask with a direct suction line (e.g., wall suction tube connectable to a wall suction port of a medical facility, or another vacuum source line). In particular, the system may be assembled by sealably connecting the airway device with the endotracheal tube or laryngeal mask immediately before removing the endotracheal tube or laryngeal mask, such that suctioning can occur through a distal end of the endotracheal tube or laryngeal mask while the device is exiting from the patient's airway. In some implementations, the distal end of the endotracheal tube or the laryngeal mask can be optionally rotated (e.g., rotated from about 30 degrees to about 180 degrees) during device removal to allow for circumferential suctioning, for example, at the posterior pharynx where secretions can accumulate. The airway adapter device may have, in particular examples described below, a generally tubular body with two fitting structures: a first fitting at one end and a second fitting at an opposite end. In some embodiments, the first fitting may be in the form of a male fitting mateable with a lumen of the wall suction tube to provide a sealed connection. Also, the second fitting may be in the form of a female fitting having a tapered lumen for connecting to the endotracheal tube or the laryngeal mask. Accordingly, in some implementations, the system or method provided herein can facilitate sealably connecting the endotracheal tube or the laryngeal mask airway to the wall suction tube to aid removal of blood and/or secretions in a patient's posterior pharynx or other portions of the patient's airway during a medical procedure (including, optionally, during the removal of the endotracheal tube, laryngeal mask, or other instrument that was previously inserted into the patient's throat as part of the anesthetic procedure or other medical procedure).

Various embodiments described herein may include a method for removing blood or bodily secretions located in a throat region. For example, the method may include disconnecting a proximal connector port of an airway device from a gas supply source in which a distal tube portion of the airway device is inserted through a patient's mouth and positioned in a patient's trachea or posterior pharynx. The method may also include releasably connecting a first end of an adapter device to the proximal connector port of the airway device by inserting the proximal connector port into a tapered lumen of the first end of the adapter device. The method may further include releasably connecting a second end of the adapter device to a vacuum source so that at least the adapter device and the distal tube portion of the airway device define a suction path to remove blood or bodily secretions located in the throat region.

In one implementation, an airway adapter device includes an elongate body defining a lumen. The body of the adapter can include a first fitting defining a tapered luminal region adapted for receiving and releasably connecting to a male type connector, and a second fitting comprising a tapered exterior configured for inserting into and releasably connecting to a female type connector.

Some embodiments of the devices provided herein include an endotracheal suction system that includes an endotracheal tube and an airway adapter device. In particular, the endotracheal tube can include an elongate tubular body extending between a distal tube portion and a proximal end port and defining a longitudinal axis. The endotracheal tube can also include a distal tube portion adapted for suctioning bodily fluids disposed in a patient's throat region. The endotracheal suction system may further include an airway adapter device. The airway adapter device can include a body having a first fitting at a first end and a second fitting at a second end. The first fitting can include a female fitting that has a cylindrical exterior and a tapered lumen adapted for receiving and sealingly mating with the proximal end port of an airway device, such as an endotracheal tube or a laryngeal mask. The second fitting can include a male fitting that includes a tapered exterior configured for insertion in a female type connector of a vacuum line.

In certain implementations, the devices provided herein include a laryngeal suction system that includes a laryngeal mask and an airway adapter device. The laryngeal mask can include an elongate tube extending between a distal elliptical mask and a proximal end port in which the elliptical mask can be configured to deploy over a patient's glottis in a posterior pharynx region. The airway adapter device can include a body including a first fitting at a first end and a second fitting at a second end. The first fitting may include a female fitting that has a cylindrical exterior, and a tapered lumen adapted for receiving and sealingly mating with the proximal end port. The second fitting may include a male fitting that has a tapered exterior and interior configured for insertion in a distal connector region of a wall suction hose. In various embodiments, the airway adapter device and the laryngeal mask are mateable together, defining at least a portion of a suction flow path for suctioning of bodily fluids disposed in a patient's throat region.

Particular embodiments of the subject matter described in this document can be implemented to optionally provide one or more of the following advantages. First, some embodiments herein may be configured to provide an efficiently connectable device for establishing a supplemental suction lumen in airway-related procedures, such as an endotracheal extubation procedure, for efficiently removing secretions and/or blood in the posterior pharynx or areas adjacent thereto immediately during the extubation procedure. Because the device can remove the excessive secretions present in the supraglottic region following an airway procedure, the use of the device can reduce the likelihood of the excessive secretions being subsequently inhaled and the consequential health complications, such as aspiration and aspiration pneumonia.

Second, some embodiments provided herein may reduce the likelihood of tissue trauma by reducing the procedure time needed to use a separate suction device (e.g., a Yankauer suction device) to remove secretions in the proximity of the larynx during an airway-related medical procedure. For example, the type of tissue trauma that may be reduced would be in regions in the mouth (e.g., the tissue of the soft or hard palate such as the palatine uvula) or pharynx (e.g., the posterior pharyngeal soft tissue). As such, in these particular implementations, the risk of tissue irritation or damage can be reduced by using airway adapter devices provided herein to provide supplemental suctioning in the throat region. Also, because the devices described herein can (in some embodiments) reduce risk of tissue irritation or damage, subsequent complications may be likewise reduced, such as larynogospasm, which is a condition of uncontrolled involuntary muscular contractions of the laryngeal cords that can lead to a blocked airway. Some embodiments of the devices described herein can minimize risk of other types of complications such as aspiration, which is the inhalation of foreign material into the lungs, for example, the inhalation of oropharyngeal or gastric contents into the lower airways.

Fourth, some implementations of the airway adapter devices provided herein can be compatible with many different airway instruments and hose connectors. For example, the airway adapted device provided herein can include a female fitting sized to fit a universal connector extending from any of a multitude of airway devices. In another example, some embodiments of the airway adapter device can include a male fitting having a tapered profile for connecting to a desired range of lumen sizes or tailored to various desired sizes of a hose, or other connector. Accordingly, the airway adapter device provided herein is designed for promoting compatibility and convenience of use regardless of the brand and/or size of the airway instruments and accessories being selected for use by particular practitioners or clinics.

The details of one or more embodiments of the invention are set forth in the accompanying drawings and the description below. Other features, objects, and advantages of the invention will be apparent from the description and drawings, and from the claims.

DESCRIPTION OF DRAWINGS

The accompanying drawings are included to provide a further understanding of the disclosure and are incorporated in and constitute a part of this specification, illustrate embodiments of the disclosure, and together with the description, serve to explain the principles of the disclosure, wherein.

Figure 1:
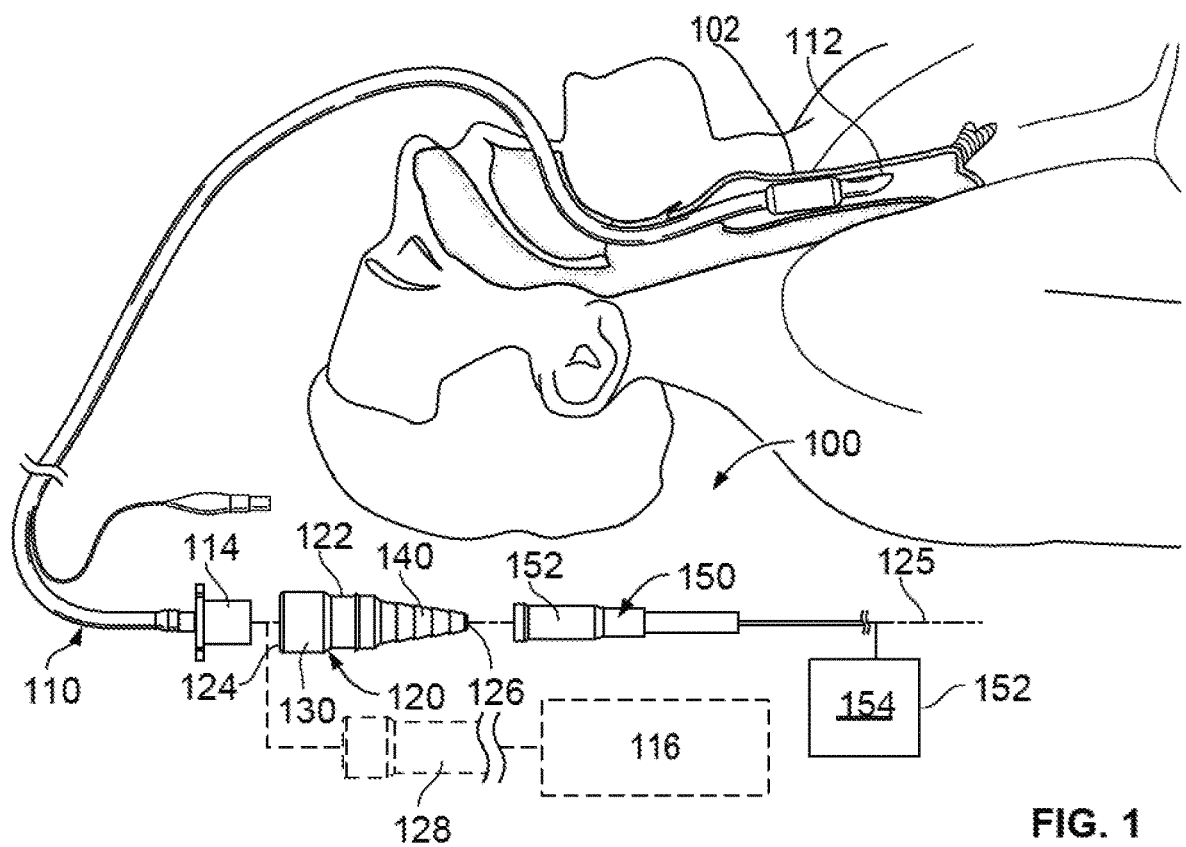
FIGS. 1-2 are side views of an endotracheal suction system that is shown in an expanded state and an assembled state, respectively, in which the assembled suction system is shown being disconnected from a gas source and attached to a vacuum source.

Like reference symbols in the various drawings may indicate like elements. It should also be noted that the accompanying drawing figures referred to herein are not all drawn to scale and may be exaggerated to illustrate various aspects of the present disclosure, and in that regard, the drawing figures should not be construed as limiting.

DETAILED DESCRIPTION

Figure 2:
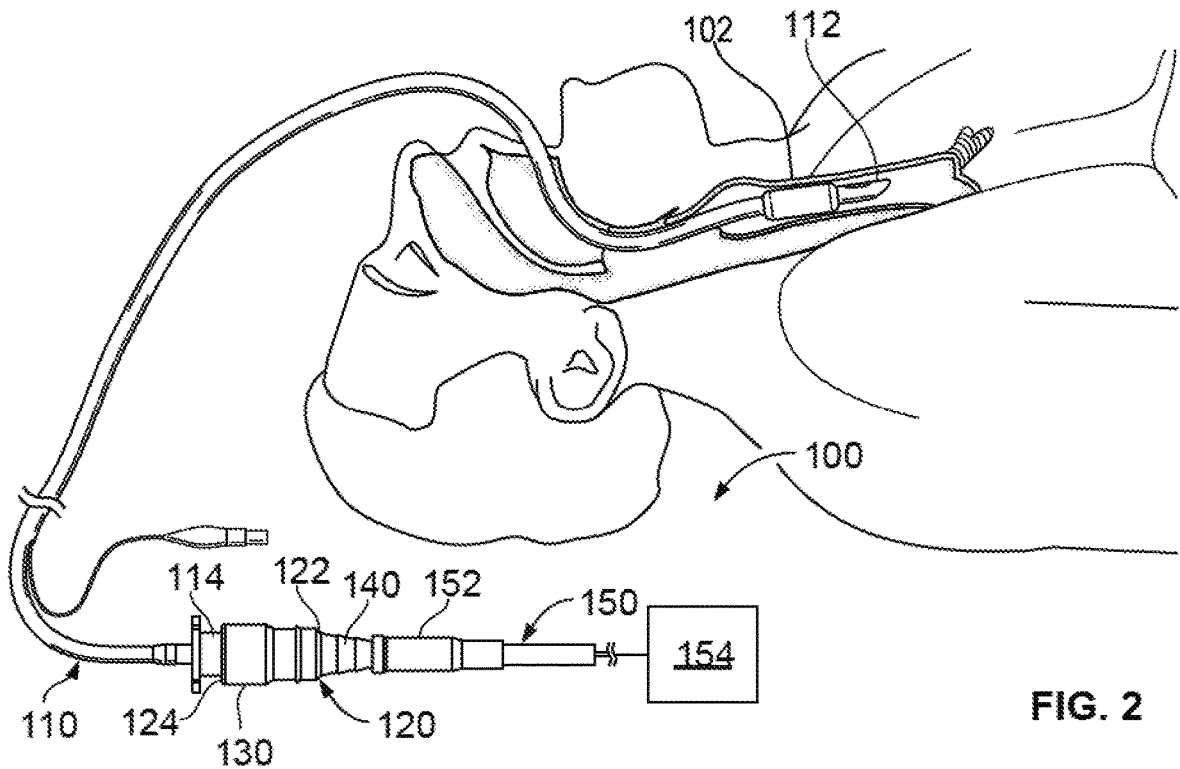
Figure 3:
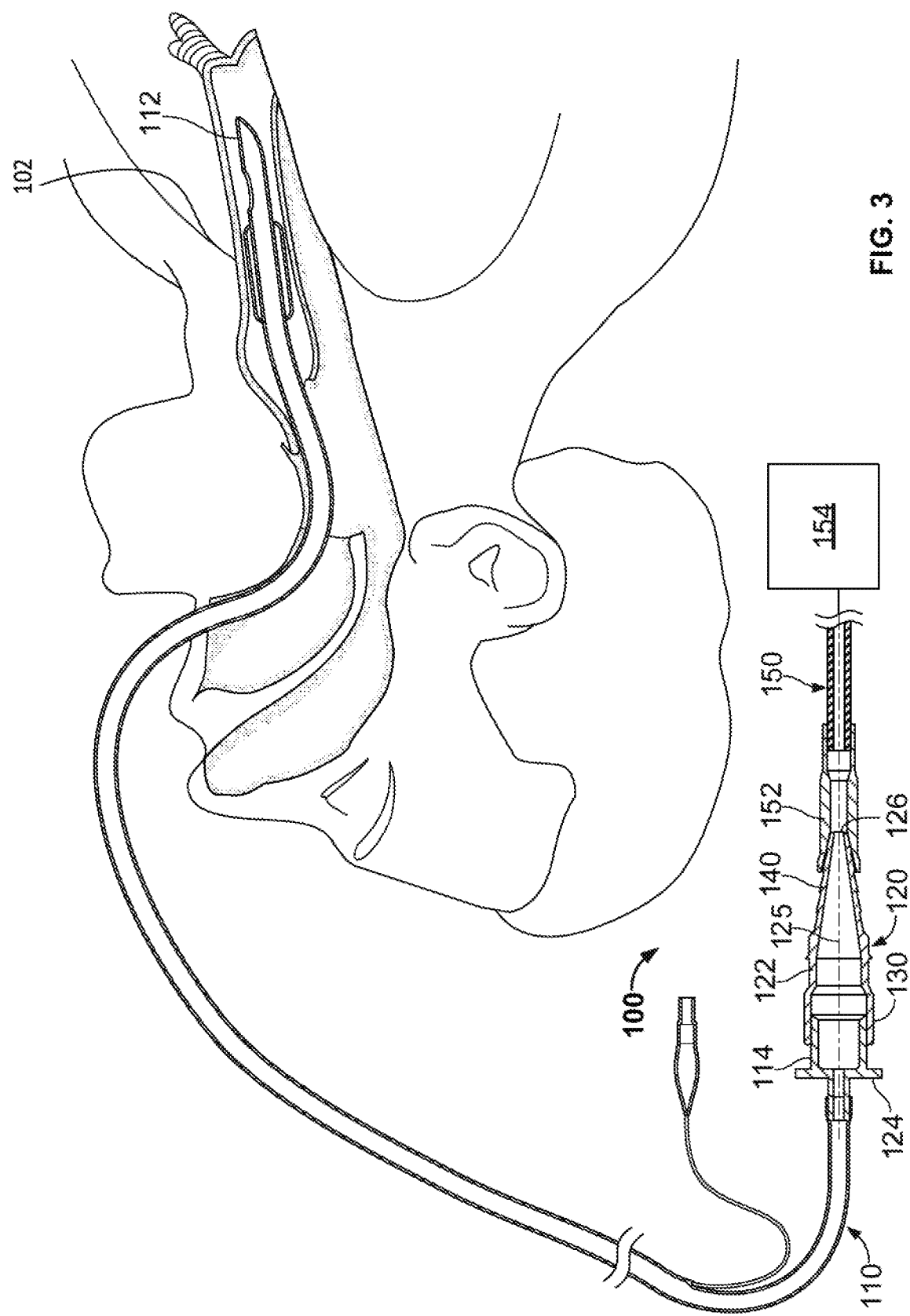
FIG. 3 is a cross-sectional side view of the endotracheal suction system of FIGS. 1-2 connected to a vacuum source.

Referring to FIGS. 1-3, some embodiments of a system 100 can provide a suction effect to a lumen of an airway device (e.g., an endotracheal tube 110 in the depicted embodiment). The endotracheal tube 110 may be used, for example, in an anesthetic procedure or other medical procedure in which a distal tube portion 112 was inserted within a trachea 102 to deliver air or other gaseous flow, such as oxygen, to a patient. For instance, the endotracheal tube 110 may have been connected to a hose attached to an anesthesia machine or system 116 to deliver an anesthesia gas to the patient. In this embodiment, the system 100 is configured to convert the distal tube portion 112 of the endotracheal tube 110 into a suction device that effectively removes blood or other deposits of bodily secretions that gathered in the throat region (including the pharynx, posterior pharynx, or both) during withdrawal of the distal tube portion 112 from the trachea 102. For example, the system 100 may be provided in the form of an endotracheal suction system 100, which comprises in the depicted embodiment at least the endotracheal tube 110 and an airway adapter device 120 configured to mate with a vacuum source (e.g., a wall suction hose 150 in the depicted embodiment, which is connectable to a wall suction port 154 of a medical facility). In some implementations, the system 100 may optionally include a wall suction hose 150 adapted for vacuum source connection.

The airway adapter device 120 provided herein can create suction capabilities in airway devices used for various medical procedures that normally establish and maintain patency of a patient's airway for ensuring sufficient exchange of oxygen and carbon dioxide. Exemplary medical procedures in which the airway adapter device 120 provided herein can be applied include medical procedures requiring mechanical ventilation, emergency medicine and general anesthesia, such as surgical procedures including gynecologic, orthopedic, urologic surgeries and the like. In some implementations, airway adapter devices 120 provided herein can be applied to various airway devices such as infraglottic airway devices (e.g., an endotracheal tube used for endotracheal intubation) and extraglottic airway devices (e.g., a laryngeal mask airway). Infraglottic airway devices are devices that pass through the glottis (i.e., enter the trachea 102) while extraglottic airway devices are devices that remain in the pharynx above the glottis and therefore do not enter the glottis. These airway devices are typically used during a medical procedure to deliver a gas having a higher concentration of oxygen as compared to air, or to administer other gases (such as helium, nitric oxide, nitrous oxide, xenon), anesthetic agents (such as desflurane, isoflurane or sevoflurane), and/or medicaments (such as salbutamol, atropine, epinephrine, ipratropium, lidocaine).

In the particular embodiment depicted in FIGS. 1-3, the airway adapter device 120 has an elongate body 122 that extends along a longitudinal axis 125 and between a first fitting 130 and a second fitting 140. Optionally, the first fitting 130 may be configured in the form of a female fitting at one end (e.g., a first end 124) of the elongate body 122, and the second fitting 140 may be configured in the form of a male fitting at the other end (e.g., a second end 126) of the body 122. As described further below, the female fitting can mechanically couple the airway adapter device 120 to the proximal end port 114 of the endotracheal tube 110. More specifically, the female fitting can be adapted for receiving and sealingly mating with a male universal fitting (e.g., the proximal end port 114 in the depicted embodiment) of the endotracheal tube 110 that is normally connected to a gas delivery tube 128 (as shown in FIG. 1) in fluid communication with the anesthesia system 116 during an anesthetic procedure or other medical procedure. At the other end of the airway adapter device 120, the male fitting (e.g., the second fitting 140) can be inserted into and mated with a distal connector region 152 of the wall suction hose 150. Accordingly, after the gas delivery tube 128 is detached from the proximal end port 114 of the endotracheal tube 110, the airway adapter device 120 can be connected to the proximal end port 114 to act as an intermediary member that defines a suction flow path from the endotracheal tube 110 to the wall suction hose 150 for removing excess bodily fluids at the periphery of the distal tube portion 112— including optionally from the patient's posterior pharynx as the distal tube portion 112 is withdrawn from the patient's throat.

In various implementations, the airway adapter device 120 can be sized and shaped to provide a press-fit design for coupling each end of the airway adapter device 120 to an airway device and/or a connector of an ancillary device or system. For instance, the airway adapter device 120 can be configured to form a press-fit connection with the depicted endotracheal tube 110 at the first end 124 and a vacuum source (e.g., distal connector region 152 of the wall suction hose 150) at the second end 126. In the depicted embodiment, the female fitting (e.g., the first fitting 130) of the airway adapter device 120 may be coupled to the male universal fitting (e.g., the proximal end port 114) of the endotracheal tube 110 by inserting the universal fitting into the female fitting of the airway adapter device 120 and manually pressing the two devices together. For instance, in some embodiments, a healthcare worker can connect the airway adapter device 120 to the endotracheal tube 110 by physically generating an axial compression force that causes the proximal end port 114 of the endotracheal tube 110 to be pressed into a lumen of the female fitting. The coupling of the male fitting (e.g., the second fitting 140) of the airway adapter device 120 can also take place by inserting the male fitting into a vacuum source connector (e.g., the distal connector region 152 of the wall suction hose 150) and pressing together the airway adapter device 120 and wall suction hose 150 using manually generated axial compression. The system 100 can be disassembled by an application of a tensile force that pulls the airway adapter device 120 away from the proximal end port 114 and optionally disconnecting the airway adapter device 120 from the distal connector region 152 of the wall suction hose 150. As such, the system 100 provided herein can be adapted for quick assembly and disassembly and, in certain implementations, optional reassembly.

Figure 4:
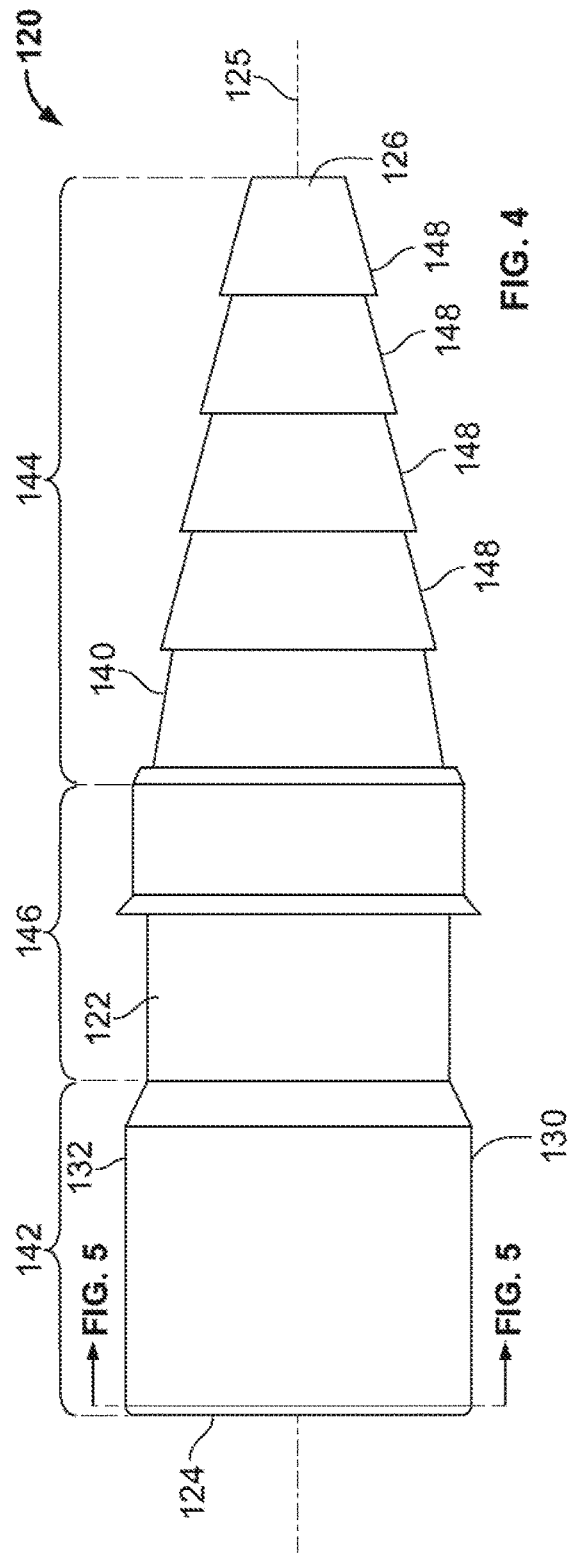
FIG. 4 is a side view of an airway adapter device of FIGS. 1-3.
Figure 5:
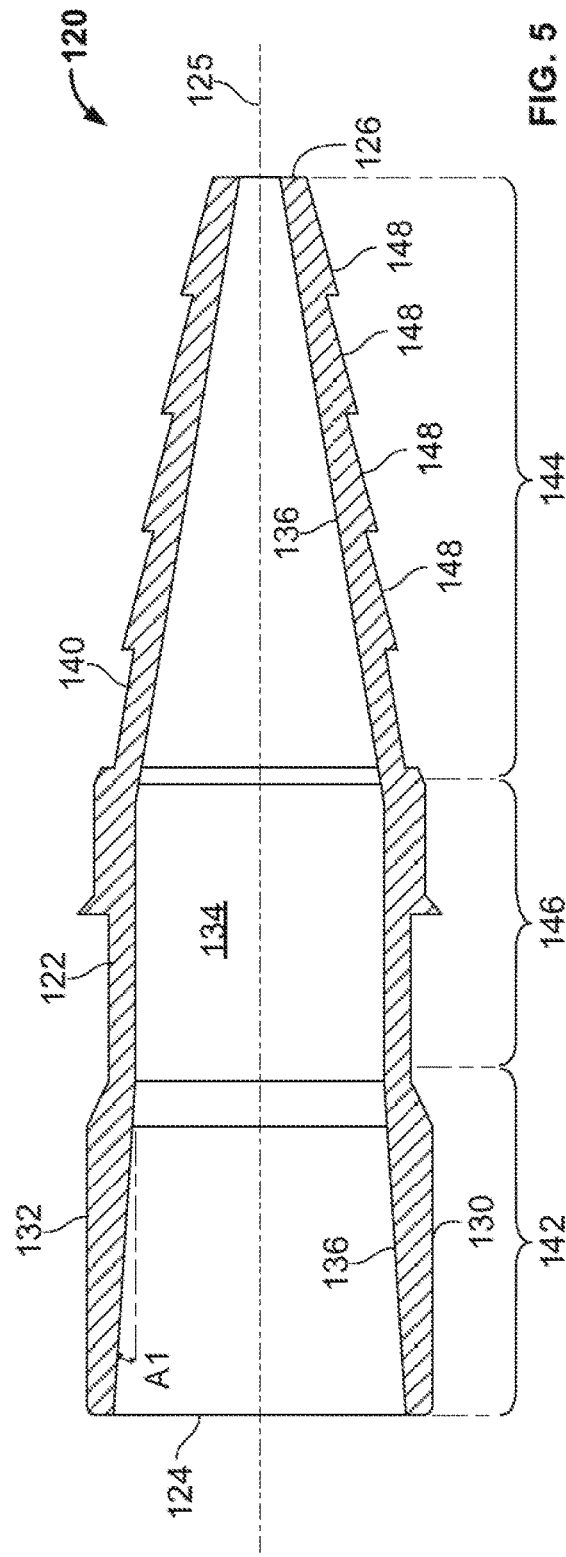
FIG. 5 is a cross-sectional side view of the airway adapter device of FIG. 4.

Referring to FIGS. 4 and 5, the airway adapter device 120 can include a first end portion 142, a second end portion 144, and a mid-portion 146 therebetween. In the depicted embodiment, the first end portion 142 of the airway adapter device 120 is formed into the first fitting 130 (e.g., a female fitting), a second end portion is formed into the second fitting 140 (e.g., a male fitting), and the mid-portion 146 has a tubular body extending between the first and second fittings 130, 140. The mid-portion 146 and end portions 142, 144 can be dimensioned, as desired, for example, to elongate the airway adapter device 120 to a suitable ergonomic length. In certain implementations, a suitable length of the mid-portion, as well as the length of the first and second end portions 142, 144, can be set based on aesthetic and/or packaging purposes. The mid-portion 146, in some embodiments, can be shaped to a suitable ergonomic cross-sectional shape that can include, but is not limited to, a curvilinear transverse cross-section such as a cylindrical or an elliptical cross-section, or a polygonal cross-section such as a rectangular cross-section.

In various implementations, the airway adapter device 120 provided herein can include distinct types of fittings on each end portion. For example, the depicted embodiment provided herein includes the first end portion 142 including the female fitting and the second end portion 144 including the male fitting. In other implementations, however, the airway adapter device 120 may include similar or identical fittings on each end. For instance, the first and second end portions 142, 144 of the airway adapter device 120 can both be formed into male fittings or, alternatively, the first and second end portions 142, 144 can both be formed into female fittings.

The airway adapter device 120 provided herein can define at least one lumen 134. In some embodiments, the lumen 134 can include luminal regions having a constant inner diameter, for example, the depicted mid-portion 146 of the airway adapter device 120 as shown in FIG. 5. At least a portion of the lumen 134 can also include a tapered lumen region 136, for example, the depicted first and second end portions 142, 144 of the airway adapter device 120. Some implementations of the lumen 134 of the airway adapter device 120 may include multiple tapered lumen regions 136, for example, two, three, four, five, or more than five tapered regions. The depicted tapered regions 136 each include an inner diameter that can transition from a larger inner diameter to a smaller, inner diameter such that the lumen decreases along at least a portion of the airway adapter device 120 in an axial direction (for example, the lumen 134 along the first end portion 142 in a proximal direction, which is depicted by an arrow in FIG. 5). The tapered lumen region 136 at one end (e.g., the first end portion 142) of the airway adapter device 120 can be a coupling surface adapted for creating a friction fit between the airway adapter device 120 and an airway device, for example, the depicted endotracheal tube 110 of FIGS. 1-3.

Still referring to FIG. 5, this depicted embodiment of the airway adapter device 120 includes the female fitting (e.g., the first fitting 130) having a generally cylindrical exterior surface 132 and a lumen 134 extending therethrough. The lumen 134 may optionally be a tapered lumen having a tapered inner diameter that gradually decreases in size as the lumen extends away from the first end 124 of the airway adapter device 120 towards the mid-portion 146 of the body 122. As such, the tapered lumen 134 can be configured to matingly receive the proximal end port 114 of an endotracheal tube (e.g., the endotracheal tube 110 of FIGS. 1-3) in a releasable friction fit engagement that provides a sealed air flow path. For example, in some embodiments, the airway adapter device 120 can include a female fitting at the first end portion 142 that can be adapted for engaging a connector of an airway device, such as the proximal end port 114 of the endotracheal tube.

To facilitate a press-fit engagement mechanism, in some embodiments, the female fitting (e.g., the first fitting 130) can have structural features that create a sealed connection when pressed together with a connector of an airway device (e.g., the proximal end port 114). Certain embodiments of the airway adapter device 120 provided herein include at least one female fitting having a tapered luminal surface adapted to receive a standard universal fitting for airway devices, e.g., a male fitting having an outer diameter of about 15 millimeters. For instance, the female fitting at the first end portion 142 of the airway adapter device 120 can be sized to include a tapered inner surface 136 configured for receiving and connecting to a male fitting (e.g., the proximal end port of an endotracheal tube, laryngeal mask or other airway device). As best seen in FIG. 5, in the depicted embodiment, the first end portion 142 has a tapered inner surface 136 shaped in the form of a frustoconical surface. The tapered inner surface 136 has a larger inner diameter at the first end 124 of the airway adapter device 120 that transitions to a smaller inner diameter as the lumen 134 extends proximally towards a mid-portion 146 of the body 122. At least a portion of the tapered inner surface 136 of the female fitting (e.g., the first fitting 130) of the airway adapter device can come into contact with the male universal fitting (e.g., the proximal end port 114 of the depicted endotracheal tube 110 of FIGS. 1-3) to create an interference fit between the airway adapter device 120 and the endotracheal tube. In particular, the female fitting and the endotracheal tube can become fastened to one another by pushing the male universal fitting into a lumen of the female fitting with sufficient compressional force to generate high frictional forces between an engaging outer surface of the universal fitting and the luminal walls of the airway adapter device 120.

In some implementations, the tapered inner surface 136 of the depicted female fitting (e.g., the first fitting 130 of the adapter device) is defined by an inner wall inclined at an angle "A1" relative to the longitudinal axis 125 of the airway adapter device 120. The angle A1 of the inner wall can be set to a suitable value for producing a frictional fit between the tapered inner surface 136 of the airway adapter 120 and an outer diameter of an airway device connector (e.g., the proximal end port 114 of the endotracheal tube). In some embodiments, the angle of the tapered inner surface 136 relative to the longitudinal axis 125 can range from about 0.5 degrees to about 60 degrees, and including all values and ranges therebetween. For instance, in certain embodiments, the angle of the tapered inner wall 136 with respect to the longitudinal axis 125 can be about 0.5 degrees, 1 degrees, 2 degrees, 3 degrees, 4 degrees, 5 degrees, 10 degrees, 15 degrees, 20 degrees, 30 degrees, 40 degrees, 60 degrees, or greater than 60 degrees.

Still referring to FIGS. 4 and 5, the depicted embodiment of the airway adapter device 120 can include the second end portion 144 having the second fitting adapted for sealingly connecting to a connector or a flexible hose being in fluid communication with a vacuum source (e.g., the distal connector region 152 of the wall suction hose 150 shown in FIGS. 1-3). For instance, in some embodiments, the second fitting 140 can be in the form of the male fitting, which is configured for insertion into a lumen of the distal connector region such that a friction fit is created between a luminal surface of the distal connector region 152 of a wall suction hose 150 and the exterior surface 132 of the second end portion 144. In some embodiments, the male fitting (e.g., the second fitting 140) may have generally frustoconical interior and exterior surfaces.

Certain implementations of the airway adapter device 120 include the male fitting (e.g., the second fitting 140) having surface features adapted for enhancing mechanical coupling between the airway adapter device 120 and a vacuum source connector, e.g., the distal connector region 152 of the wall suction hose 150 of FIGS. 1-3. Optionally, in some embodiments, the male fitting of the airway adapter device 120 can include one or more barbed elements along the exterior of the body 122 for securing the airway adapter device 120 to the wall suction hose 150. In some embodiments, the airway adapter device 120 can include one, two, three, four, five, or more than five barbed elements 148. Multiple barbed elements 148 may be positioned along the frustoconical exterior surface such that each barb 148 optionally has a different maximum outer diameter, allowing the airway adapter device 120 to be compatible with a range of different connector (or tubing) sizes. Certain implementations of the male fitting (e.g., the second fitting 140) include barbed elements having maximum outer diameters that can range from about 5 mm to about 11 mm (or about 3/16 inches to about 7/16 inches). For example, the depicted second end portion 144 of the airway adapter device 120 can optionally include at least five barbed elements having a maximum outer diameter of about 3/16 inches, 3/8 inches, 7/16 inches, 1/2 inches and 9/16 inches. In some implementations, the male fitting can have a textured or irregular exterior surface, such as a roughened surface or a threaded or knurled surface. In other embodiments, as will be discussed with FIGS. 8 and 9, the male fitting portion (e.g., the second end portion 144) does not include a textured surface.

The airway adapter devices 120 provided herein are scalable to a range of sizes. Certain embodiments of the airway adapter device 120 include dimensions (such as length, diameter, or width) adapted for providing a user, such as a healthcare worker, with an ergonomic gripping area. The overall length "L" of the airway adapter device 120 can be optionally sized for inclusion within product packaging that includes both the airway adapter device 120 and a compatible airway product (e.g., the endotracheal tube 110 or a laryngeal mask) or, alternatively, only the airway adapter device 120. In some implementations, the adapter device 120 can include an overall length that can range from about 30 mm to about 100 mm, including all values and ranges therebetween. For example, embodiments of the adapter device 120 may include an overall length L of about 30 mm, 35 mm, 40 mm, 45 mm, 50 mm, 55 mm, 60 mm, 65 mm, 70 mm, 75 mm, 80 mm, 90 mm, 100 mm, 110 mm, 120 mm, 130 mm, 140 mm, 150 mm, 160 mm, 170 mm, 180 mm, 190 mm, 200 mm, or greater than 200 mm. Some embodiments of the adapter device 120 include an outer diameter "OD" that can range between about 6 mm and about 20 mm (e.g., a minimum outer diameter of about 6 mm and a maximum outer diameter of about 20 mm). A suitable outer diameter OD can range from about 2 mm to about 30 mm, about 5 mm to about 25 mm, about 10 mm to about 20 mm, about 2 mm to about 25 mm, about 2 mm to about 20 mm, about 5 mm to about 30 mm, about 5 mm to about 20 mm, about 10 mm to about 30 mm, about 10 mm to about 25 mm, about 10 mm to about 20 mm, about 20 mm to about 25 mm, about 25 mm to about 30 mm, about 20 mm to about 30 mm, about 30 mm to about 40 mm, about 40 mm to about 50 mm, or about 50 mm to about 60 mm. The adapter device 120 provided herein can include an inner diameter "ID" that can range from about 2 mm to about 25 mm, including all values and ranges therebetween. For example, in some cases, the adapter device 120 can have a minimum inner diameter of about 6 mm and a maximum outer diameter of about 20 mm. A suitable inner diameter ID can range from about 3 mm to about 25 mm, about 5 mm to about 20 mm, about 7 mm to about 16 mm, about 3 mm to about 20 mm, about 3 mm to about 16 mm, about 5 mm to about 25 mm, about 5 mm to about 16 mm, about 7 mm to about 25 mm, about 7 mm to about 20 mm, about 16 mm to about 20 mm, or about 20 mm to about 25 mm, in some embodiments.

In some implementations, the female fitting can have a maximum inner diameter that ranges from about 15.0 mm to about 16.0 mm and a minimum inner diameter that ranges from about 14.5 to about 15.5. Some embodiments of the airway adapter device 120 can include a female fitting (e.g., the first fitting 130) having an inner diameter that tapers from about 15.5 mm to about 15.0 mm (i.e., the maximum diameter of the female fitting is about 15.5 mm and the minimum diameter is about 15.0 mm).

The airway adapter device 120 provided herein can be made of various materials, including polymer, metal and/or ceramic materials. In some embodiments, the airway adapter device 120 is composed of a polymeric material, such as a thermoplastic or a thermoset polymer. Suitable polymers for forming the airway adapter device 120 can include, but are not limited to, polycarbonate, polyethylene, polypropylene, polyvinylchloride, polyethylene terephthalate, polyether ether ketone, polyvinylchloride, nylon, polytetrafluoroethylene, polyurethane, silicone and combinations thereof.

Some embodiments of the airway adapter device 120 can include a single-piece body. In other embodiments, airway adapter devices 120 can be assembled from multiple components. Various processing methods can be used to fabricate the airway adapter devices provided herein. For example, the body 122 of the airway adapter device 120 may be fabricated using a thermoplastic processing technique such as, but not limited to, injection molding, extrusion, dip coating, spraying and the like. In certain implementations, multi-component bodies can be made by joining together two or more components by applying a joining technique, such as, but not limited to, adhesive bonding, heat bonding, laser bonding, press-fitting, and the like, as well as combinations thereof.

Figure 6:
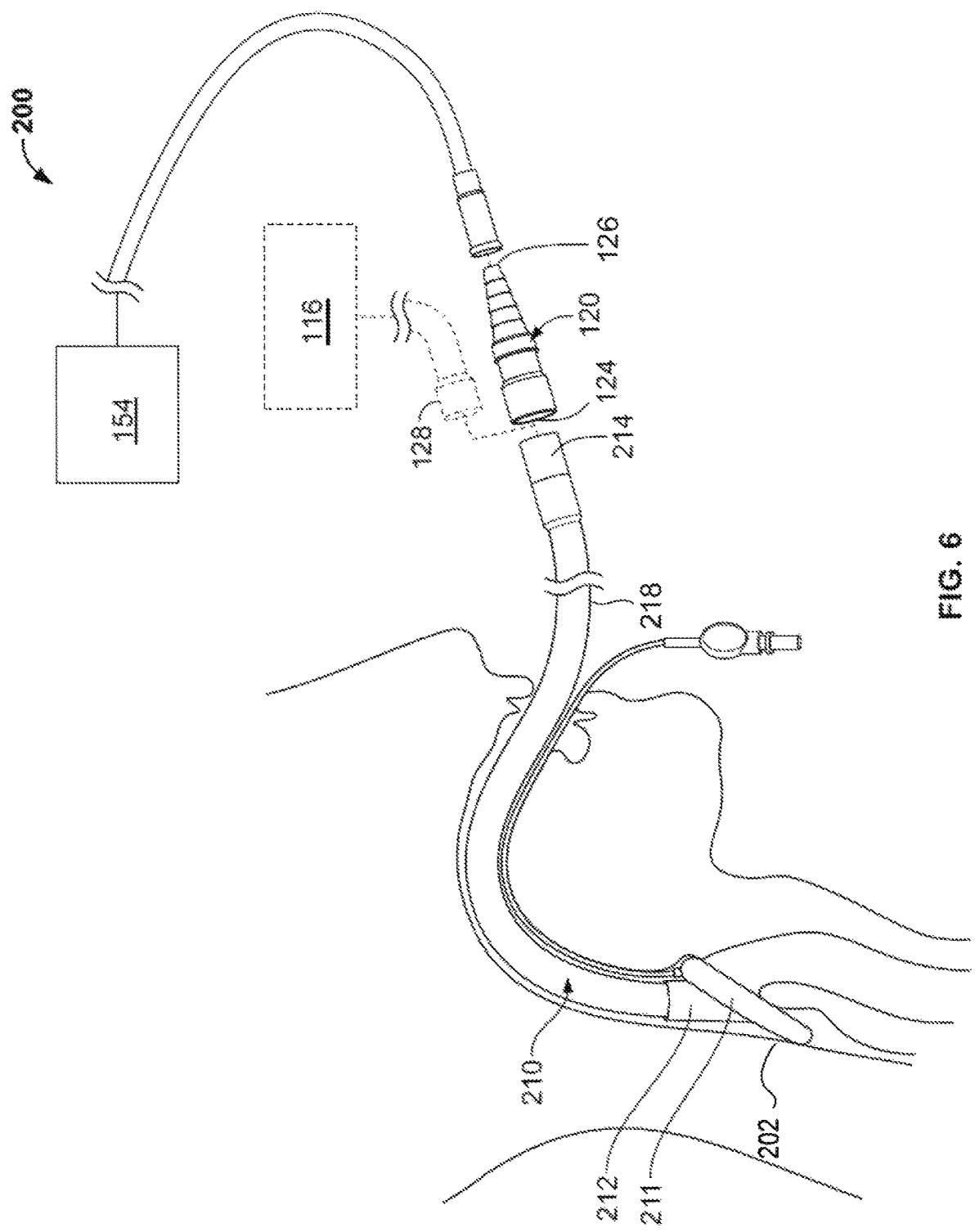
FIGS. 6 and 7 are side views of a laryngeal mask suction system that is shown in an expanded state and an assembled state, respectively, in which the assembled suction system is shown being disconnected from a gas source and being attached to a vacuum source.
Figure 7:
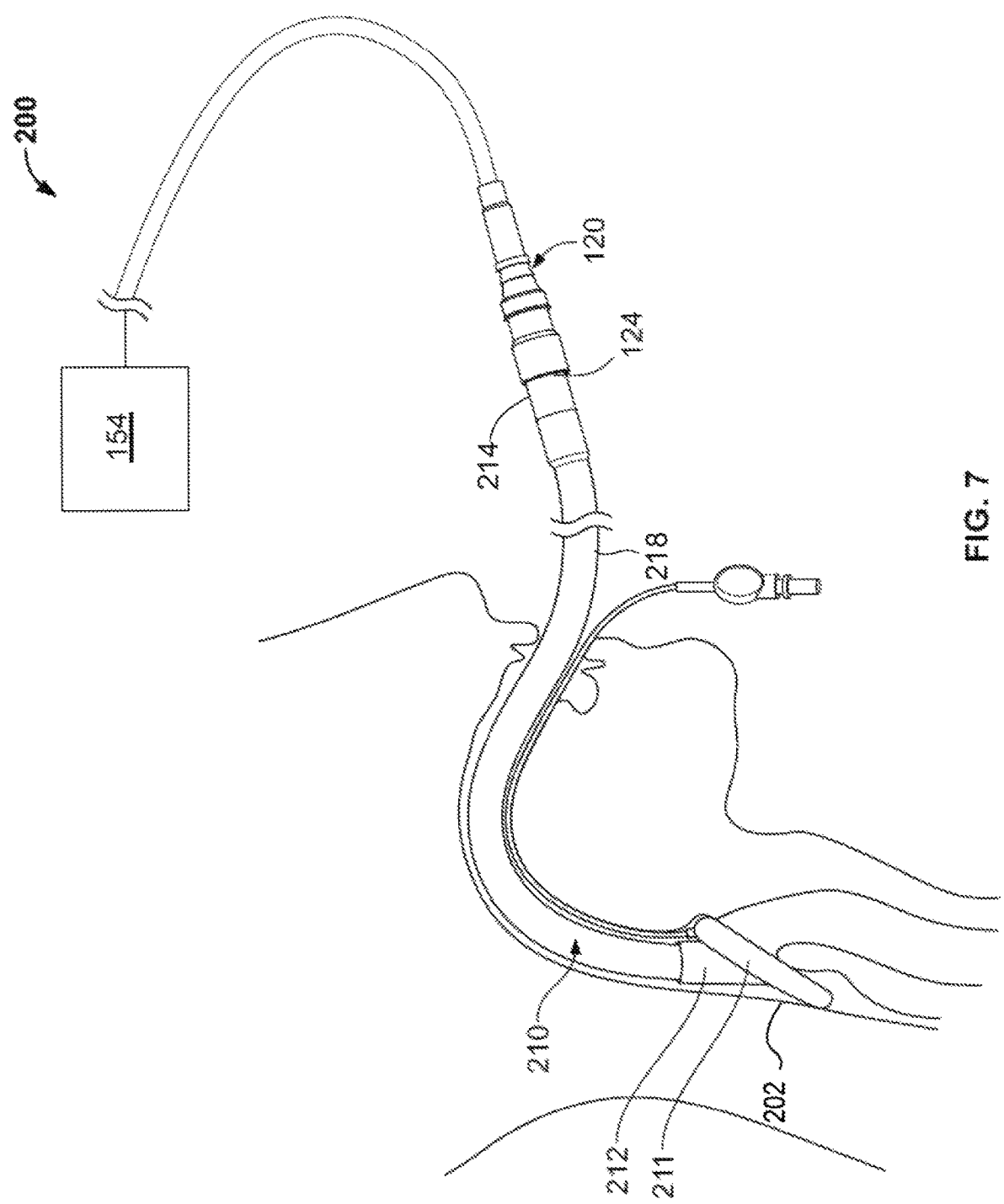

Referring to FIGS. 6 and 7, another embodiment of a system 200 can provide a suction effect to an elliptical mask 211 of a depicted laryngeal mask 210. The laryngeal mask 210 may be applicable, for example, in an anesthetic procedure or other medical procedure in which the elliptical mask 211 at a distal end portion 212 of the laryngeal mask 210 was inserted through the patient's mouth and deployed over the glottis in the posterior pharynx region 202. Following deployment, the laryngeal mask 210 delivered air or other gaseous flow, such as anesthesia gas, air, or oxygen, to a patient through an airway tube 218 and the elliptical mask 211. The laryngeal mask 210 may have been connected to a hose 128 attached to a gas source, such as an anesthesia system 116 or a gas supply (e.g., oxygen supply tank), to deliver gaseous flow to the patient. In the depicted embodiment, the system 200 is configured to convert the elliptical mask 211 of the laryngeal mask 210 into a suction device that effectively removes blood or other deposits of bodily secretions that gathered in the throat region (including the pharynx, posterior pharynx 202, or both) prior to and upon withdrawing the laryngeal mask 210 from the patient's throat.

In some embodiments, the system 200 can include a laryngeal mask suction system that can be assembled after an airway procedure and before the removal of the airway devices, such as the laryngeal mask 210. Prior to assembling the system 200, the laryngeal mask 210 can be optionally disconnected from a gas source (e.g., the anesthesia system 116) and connecting the laryngeal mask 210 to an adapter 120 that is releasably couplable to a vacuum source (e.g., wall suction port 154). For example, a proximal end port 214 of the laryngeal mask 210 may be disconnected from the gas source (e.g., the anesthesia system 116). The proximal end port 214 of the laryngeal mask 210 can subsequently be connected to one end (e.g., a first end 124) of the airway adapter device 120, which can optionally be fastened at the other end (e.g., the second end 126) to the vacuum source, such as a wall suction port 154. The exemplary system 200 may be provided in the form of a laryngeal mask system 200, which comprises in the depicted embodiment at least the laryngeal mask 210 and the airway adapter device 120 configured to mate with the vacuum source (e.g., a wall suction hose 150 in the depicted embodiment).

Figure 8:
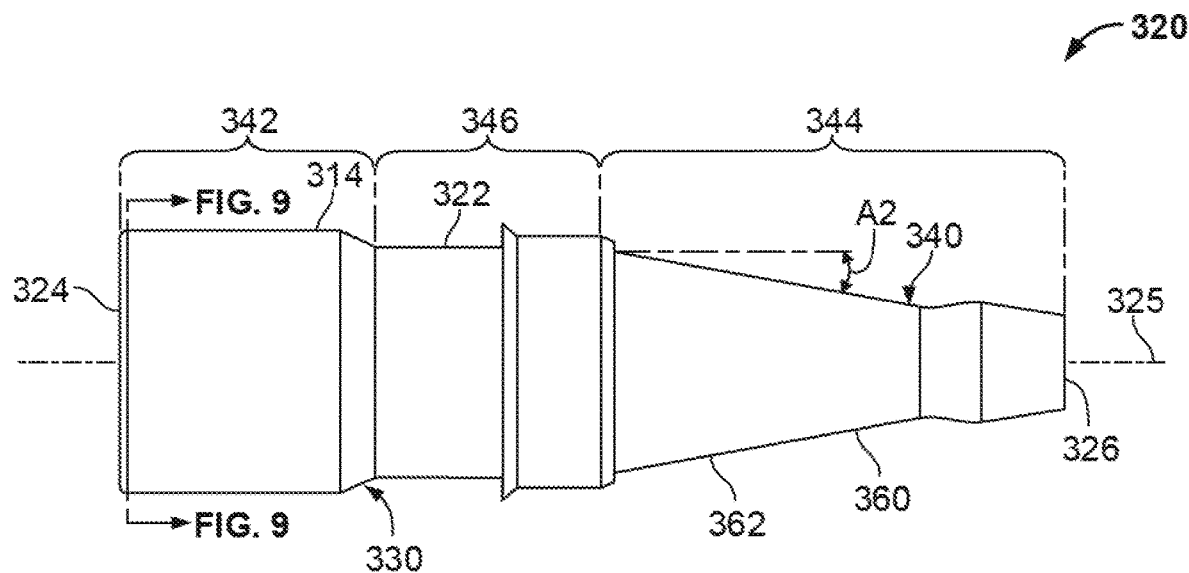
FIG. 8 is a side view of a second exemplary airway adapter device.
Figure 9:
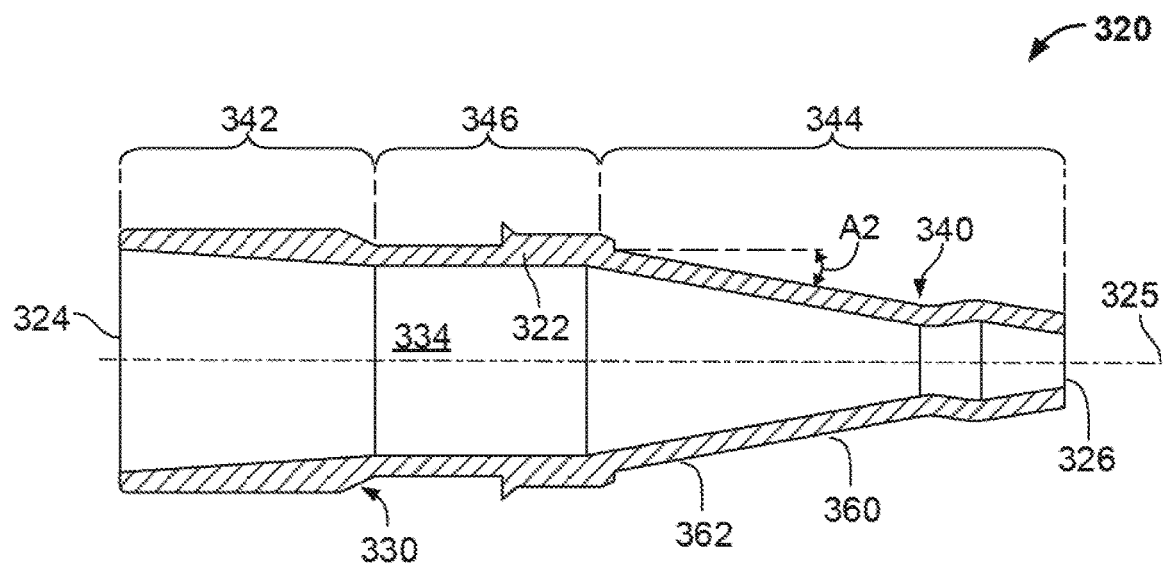
FIG. 9 is a cross-sectional side view of the airway adapter device of FIG. 8.

Referring to FIGS. 8 and 9, a second exemplary airway adapter device 320 has an elongate body 322 that extends along a longitudinal axis 325 between a first end 324 and a second end 326 and defines a lumen 334 extending therethrough. The airway adapter device 320 also includes a first end portion 342 that has a first fitting 330, and a second end portion 344 that has a second fitting 340. In some embodiments, the first and second fittings 330, 340 of the airway adapter device 320 can be formed into female and male fittings, respectively. The depicted embodiment includes a male fitting formed in the second end portion 344 that has a smooth tapered outer profile 360 for facilitating a sealing connection between the airway adapter device 320 and a wall suction hose (e.g., the wall suction hose 150 of FIGS. 1-3). The tapered outer profile 360 is adapted to facilitate releasable attachment of the airway adapter device 320 to connectors having a range of various inner diameters. Unlike the airway adapter device 120 of FIGS. 1-7, the depicted airway adapted device 320 does not have barbed features (e.g., barbed elements 148 of FIGS. 4 and 5) along an exterior surface 362. Instead, the tapered outer profile 360 can be adapted by its size and shape to releasably attach through an interference fit to a flexible connector (e.g., a distal connector region 152 of a wall suction hose 150 of FIGS. 1-3) that connects to a vacuum source, such as a wall suction port (e.g., the wall suction port 154 of FIGS. 1-3, 6 and 7). For instance, in some cases, the tapered outer profile 360 of the male fitting can be defined by at least a portion of the exterior surface 362 being oriented at an angle "A2" relative to the longitudinal axis 325. In some embodiments, the angle A2 of the exterior surface relative to the longitudinal axis 325 can range from about 0.5 degrees to about 60 degrees, and including all values and ranges therebetween. For instance, in certain embodiments, the angle A2 of the exterior surface 362 may be about 0.5 degrees, 1 degrees, 2 degrees, 3 degrees, 4 degrees, 5 degrees, 10 degrees, 15 degrees, 20 degrees, 30 degrees, 40 degrees, 60 degrees, or greater than 60 degrees.

Figure 10:
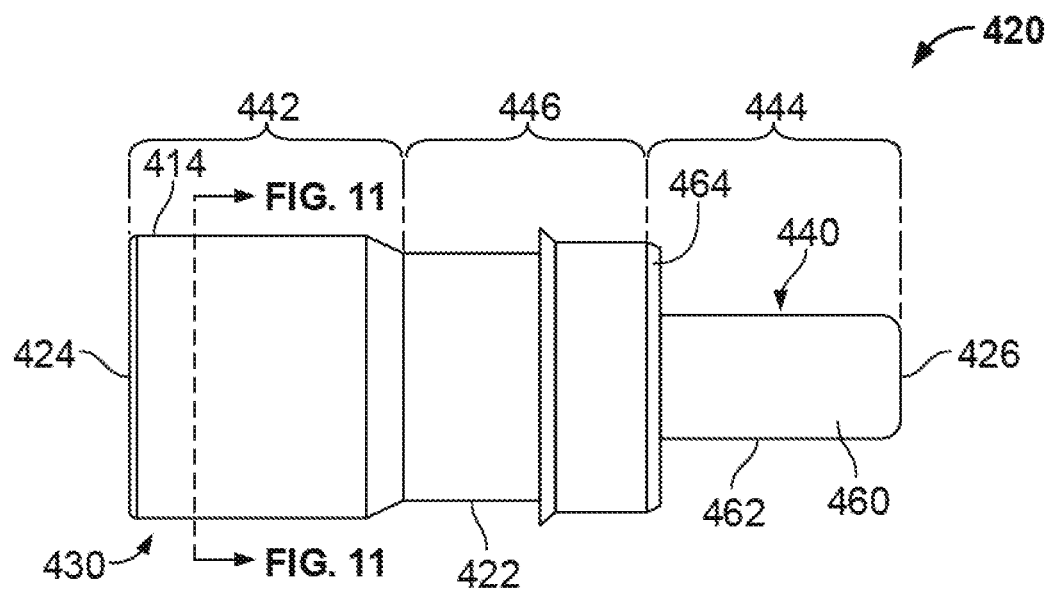
FIG. 10 is a side view of a third exemplary airway adapter device.
Figure 11:
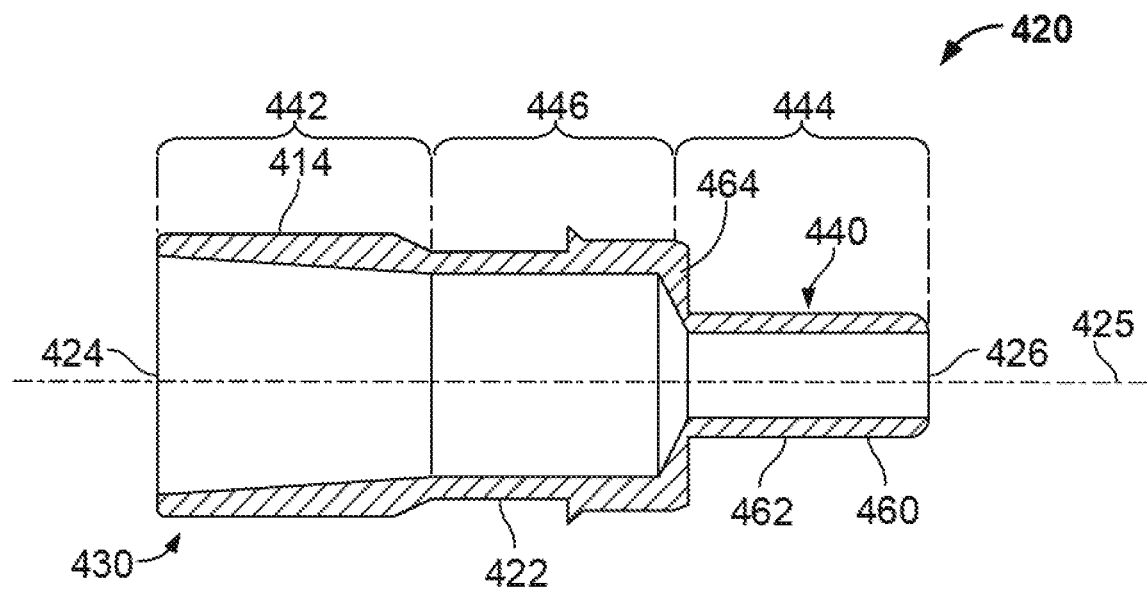
FIG. 11 is a cross-sectional side view of the airway adapter device of FIG. 10.

Referring to FIGS. 10 and 11, a third exemplary airway adapter device 420 has a body 422 that extends along a longitudinal axis 425 between a first fitting 430 and a second fitting 440. The depicted first fitting 430 is formed into a female fitting at a first end portion 442 of the body 422, and the second fitting 440 is formed into a male fitting at the second end portion 444 of the body 422. The airway adapter device 420 is similar to the previous airway adapter devices 120, 320 with exception of the male fitting design (e.g., the second fitting 440).

At the second end 426 of the airway adapter device 420, the male fitting (e.g., the second fitting 440) can be inserted into and mated to a connector, such as the distal connector region 152 of the wall suction hose 150 of FIGS. 1-3. In some embodiments, the exterior surface 462 of the second fitting 440 has a stepped profile 464 that includes a stepped outer diameter region in which the outer diameter significantly reduces from a larger outer diameter to a smaller outer diameter. In certain implementations, the stepped profile 464 can adjust an outer profile of the second fitting to facilitate securement with a connector lumen. In some embodiments, the outer profile of the male fitting (e.g., the second fitting 440) at the second end 426 of the body can be a tubular end portion 460 adapted for forming a friction-fit connection with a specific diameter hose. As such, the tubular end portion 460 can be press fitted into a lumen of a connector (e.g., the distal connector region 152 of the wall suction hose 150 of FIGS. 1-3). In some implementations, the tubular end portion 460 can provide for an improved secured attachment between the airway adapter device 420 and a connector that allows for a fluid connection with a vacuum source.

Still referring to FIGS. 10 and 11, the female fitting (e.g., the first fitting 430) of the depicted airway adapter device 420 can mechanically couple the airway adapter device 420 to another airway device, such as the endotracheal tube 110 of FIGS. 1-3, similar to previously discussed female fittings (e.g., the first fittings 130, 330) provided herein. As such, the airway adapted device 420 at the first end portion 442 can be adapted for receiving and sealingly mating with a male universal fitting (e.g., the proximal end port 114 as shown in FIGS. 1-3) of the other airway device, such as the endotracheal tube 110 or the laryngeal mask.

A number of embodiments of the invention have been described. Nevertheless, it will be understood that various modifications may be made without departing from the scope of the invention. Accordingly, other embodiments are within the scope of the following claims.

What is claimed is:

1. A method of removing blood or bodily secretions located in a throat region, the method comprising:
    inserting a distal tube portion of an endotracheal tube through a patient's mouth to be positioned in a trachea or posterior pharynx of the patient;
    connecting a breathable gas supply source to a proximal connector port of the endotracheal tube to deliver breathable gas from the breathable gas supply source through the distal tube portion of the endotracheal tube;
    disconnecting the proximal connector port of the endotracheal tube from the breathable gas supply source while the distal tube portion of the endotracheal tube remains inserted through the patient's mouth and positioned in the trachea or posterior pharynx;
    after the disconnecting the proximal connector port of the endotracheal tube from the breathable gas supply source, releasably connecting a first end of a suction adapter device to the proximal connector port of the endotracheal tube by inserting the proximal connector port into a tapered lumen of the first end of the suction adapter device while the distal tube portion of the endotracheal tube remains positioned in the trachea or posterior pharynx;
    releasably connecting a second end of the suction adapter device to a vacuum source while the distal tube portion of the endotracheal tube is positioned in the trachea or posterior pharynx so that at least the suction adapter device and the distal tube portion of the endotracheal tube define a suction path to remove the blood or bodily secretions in the throat region, the suction adapter device comprising a continuous sealed passage between the first end and the second end of the suction adapter device; and
    removing the blood or bodily secretions in the throat region through the endotracheal tube and the suction adapter device while withdrawing the distal tube portion of the endotracheal tube from the patient's throat.

2. The method of claim 1, wherein the withdrawing the distal tube portion of the endotracheal tube from the patient's throat comprises rotating the endotracheal tube.

3. The method of claim 2, further comprising providing a fluid connection path between the suction adapter device and a wall suction source while the distal tube portion of the endotracheal tube is positioned in the trachea posterior pharynx.

4. The method of claim 3, wherein the releasably connecting the proximal connector port of the endotracheal tube to the tapered lumen comprises engaging the tapered lumen of the suction adapter device with the proximal connector port of the endotracheal tube in a releasable friction fit that provides a sealed air flow path between the suction adapter device and the endotracheal tube.

5. The method of claim 4, wherein the tapered lumen has a tapered inner surface defined by an inner wall inclined at an angle relative to a longitudinal axis of the suction adapter device.

6. The method of claim 5, wherein the angle of the tapered inner surface relative to the longitudinal axis ranges from about 0.5 degrees to about 5 degrees.

7. The method of claim 6, wherein the angle of the inner wall is adapted for producing a frictional fit between the tapered inner surface of the suction adapter device and an outer diameter of the proximal connector port of the endotracheal tube.

8. The method of claim 7, wherein the second end of the suction adapter device comprises a male fitting having barbed elements, and releasably connecting a distal connector of a suction hose to the second end of the suction adapter device by releasably connecting the distal connector of the suction hose to the male fitting of the suction adapter device, wherein maximum diameters of the barbed elements are different from one another.

9. The method of claim 6, wherein the suction adapter device comprises a second tapered lumen at the second end, wherein the second tapered lumen has a tapered interior surface defined by an interior wall inclined at an angle relative to the longitudinal axis of the suction adapter device, wherein the angle of the tapered interior surface of the second tapered lumen relative to the longitudinal axis is greater than the angle of the tapered inner surface of the first end of the suction adapter device.

10. The method of claim 1, wherein upon the releasably connecting of the second end of the suction adapter device to the vacuum source, a sealed suction path is created while the distal tube portion of the endotracheal tube is positioned in the trachea or posterior pharynx.

11. The method of claim 1, wherein the proximal connector port is a standard universal fitting for endotracheal devices.

12. The method of claim 1, wherein the second end of the suction adapter device comprises a tapered exterior defining a tapered region having an inner diameter that transitions from a larger inner diameter to a smaller inner diameter such that the tapered region decreases along at least a portion of the suction adapter device in an axial direction along the second end.

13. A method of removing blood or bodily secretions located in a throat region, the method comprising:
    inserting a distal tube portion of a laryngeal mask through a patient's mouth to be positioned in a posterior pharynx region of the patient;
    connecting a breathable gas supply source to a proximal connector port of the laryngeal mask to deliver breathable gas from the breathable gas supply source through the distal tube portion of the laryngeal mask;
    disconnecting the proximal connector port of the laryngeal mask from the breathable gas supply source while a distal elliptical mask of the laryngeal mask remains inserted through the patient's mouth and is deployed over a glottis of the patient in the posterior pharynx region;
    after disconnecting the proximal connector port of the laryngeal mask from the breathable gas supply source, releasably connecting a first end of a suction adapter device to the proximal connector port of the laryngeal mask by inserting the proximal connector port into a tapered lumen of the first end of the suction adapter device while the distal tube portion of the laryngeal mask remains positioned in the posterior pharynx region;
    releasably connecting a second end of the suction adapter device to a vacuum source while the distal elliptical mask of the laryngeal mask is positioned in the posterior pharynx region so that at least the suction adapter device and the distal tube portion of the laryngeal mask define a suction path to remove the blood or bodily secretions in the throat region, the suction adapter device comprising a continuous sealed passage between the first end and the second end of the suction adapter device; and
    removing the blood or bodily secretions in the throat region through the laryngeal mask and the suction adapter device while withdrawing the distal tube portion of the laryngeal mask from the patient's throat.

14. The method of claim 13, wherein the withdrawing distal tube portion of the laryngeal mask from the patient's throat comprises rotating the laryngeal mask.

15. The method of claim 14, further comprising providing a fluid connection path between the suction adapter device and a wall suction source while the distal elliptical mask of the laryngeal mask is deployed over the patient's glottis.

16. The method of claim 15, wherein the releasably connecting the proximal connector port of the laryngeal mask to the tapered lumen comprises engaging the tapered lumen of the suction adapter device with the proximal connector port of the laryngeal mask in a releasable friction fit that provides a sealed air flow path between the suction adapter device and the laryngeal mask.

17. The method of claim 16, wherein the tapered lumen has a tapered inner surface defined by an inner wall inclined at an angle relative to a longitudinal axis of the suction adapter device.

18. The method of claim 17, wherein the angle of the tapered inner surface relative to the longitudinal axis ranges from about 0.5 degrees to about 5 degrees.

19. The method of claim 18, wherein the angle of the inner wall is adapted for producing a frictional fit between the tapered inner surface of the suction adapter device and an outer diameter of the proximal connector port of the laryngeal mask.

20. The method of claim 19, wherein the second end of the suction adapter device comprises a male fitting having barbed elements, and releasably connecting a distal connector of a suction hose to the second end of the suction adapter device by releasably connecting the distal connector of the suction hose to the male fitting of the suction adapter device, wherein maximum diameters of the barbed elements are different from one another.

21. A method of removing blood or bodily secretions located in a throat region in a patient, the method comprising:
    inserting a distal tube portion of an endotracheal tube through a patient's mouth to be positioned in a trachea or posterior pharynx of the patient;
    connecting a breathable gas supply source to a standard universal fitting of the endotracheal tube to deliver breathable from the gas supply source through the distal tube portion of the endotracheal tube;
    disconnecting the standard universal fitting of the endotracheal tube from the breathable gas supply source while the distal tube portion of the endotracheal tube remains inserted through the patient's mouth and positioned in the trachea or posterior pharynx;

after the disconnecting the standard universal fitting of the endotracheal tube from the breathable gas supply source, releasably connecting a female fitting of a suction adapter device that is adapted to receive the standard universal fitting of the endotracheal tube by inserting the standard universal fitting into the female fitting of the suction adapter device while the distal tube portion of the endotracheal tube remains positioned in the trachea or posterior pharynx, wherein female fitting has a tapered luminal surface that provides a press-fit connection adapted for quick connection and disconnection to the endotracheal tube;

releasably connecting a male fitting of the suction adapter device to a vacuum source while the distal tube portion of the endotracheal tube is positioned in the trachea or posterior pharynx so that at least the suction adapter device and the distal tube portion of the endotracheal tube define a suction path to remove the blood or bodily secretions in the throat region, wherein the male fitting has a tapered exterior surface, the suction adapter device comprising a continuous sealed passage between the female fitting and the male fitting of the suction adapter device; and removing blood or bodily secretions in the patient's posterior pharynx or other portions of the patient's airway through the endotracheal tube and the suction adapter device while withdrawing the distal tube portion of the endotracheal tube from the patient's throat.

* * * * *

UNITED STATES PATENT AND TRADEMARK OFFICE
CERTIFICATE OF CORRECTION

PATENT NO. : 12,239,786 B2
APPLICATION NO. : 17/005707
DATED : March 4, 2025
INVENTOR(S) : Hoyt Nye Page 1 of 1

It is certified that error appears in the above-identified patent and that said Letters Patent is hereby corrected as shown below:

In the Claims

Column 12, Line 63, Claim 3, after "trachea" please insert -- or --.

Signed and Sealed this
Twenty-second Day of July, 2025

Coke Morgan Stewart
*Acting Director of the United States Patent and Trademark Office*